United States Patent [19]

Yeung

[11] Patent Number: 5,895,395
[45] Date of Patent: Apr. 20, 1999

[54] PARTIAL TO FULL THICKNESS SUTURE DEVICE & METHOD FOR ENDOSCOPIC SURGERIES

[76] Inventor: Teresa T. Yeung, 834 N. White Rd., San Jose, Calif. 95127

[21] Appl. No.: 08/896,106

[22] Filed: Jul. 17, 1997

[51] Int. Cl.$^6$ .............................................. A61B 17/04
[52] U.S. Cl. ........................... 606/144; 606/139; 606/148
[58] Field of Search ................................. 606/139, 144, 606/148

[56] References Cited

U.S. PATENT DOCUMENTS

| | | | |
|---|---|---|---|
| 659,422 | 10/1900 | Shildler | 606/144 |
| 3,856,009 | 12/1974 | Winnie | 128/214.4 |
| 4,493,323 | 1/1985 | Albright et al. | 606/144 |
| 4,511,356 | 4/1985 | Froning et al. | 604/164 |
| 4,884,572 | 12/1989 | Bays et al. | 128/334 R |
| 4,895,148 | 1/1990 | Bays et al. | 606/213 |
| 5,026,350 | 6/1991 | Tanaka et al. | 604/158 |
| 5,037,433 | 8/1991 | Wilk et al. | 606/139 |
| 5,059,206 | 10/1991 | Winters | 606/213 |

(List continued on next page.)

OTHER PUBLICATIONS

Johnson, L.L., 1986, Arthroscopic Surgery: Principles & Practice.
Siliski, J.M., 1994, Traumatic Disorders of the Knee.
Ed: Aichroth, P et al, 1992 Knee Surgery: Current Practice.
Fu, F. et al, Knee Surgery Vol.I.

*Primary Examiner*—Gary Jackson

[57] ABSTRACT

This invention relates to devices and methods for making partial thickness or full thickness sutures in tissues endoscopically. The preferred embodiment comprises a suture delivering needle and a suture receiving needle which are in substantially parallel alignment. A shape memory needle with a pre-formed semi-circular shape is used to bridge a gap formed between the suture delivery needle and receiving needle. In preparation for a surgical procedure, the shape memory needle is retracted and partially straightened in the suture delivering needle. After determining the placement of suture, the suture delivering and suture receiving needles are pierced into the repairing tissue. The semi-circular shape memory needle is deployed and resumes the appropriate pre-formed shape while piercing the tissue and extending into the distal opening of the suture receiving needle. A suture is then passed down from the proximal opening of the shape memory needle into the distal opening of the suture receiving needle, then out of the proximal opening of the receiving needle. The shape memory needle is then retracted back into the suture delivering needle, leaving only the suture bridging the distal openings of the delivery needle and receiving needle. The suture device is then withdrawn and the suture is tied to fasten the tissue.

| NUMERAL REFERENCES IN DRAWINGS | |
|---|---|
| Suture Delivering Needle (SDN) | 1 |
| SDN Distal Opening | 2 |
| Gliding Slot | 3 |
| Trough | 4 |
| Strain, Stress Relief Window (SRW) | 5 |
| Endoscopic Scissors | 6 |
| Shape Memory Needle (SMN) | 7 |
| SMN Distal Opening | 8 |
| SMN Proximal Beveled Opening | 9 |
| Suture Receiving Needle (SRN) | 10 |
| SRN Distal Opening | 11 |
| Receiving Slot for SMN | 12 |
| Penetration Markers | 13 |
| Body | 14 |
| Equipment Inlet | 15 |
| Equipment Outlet | 16 |
| Operating Lever | 17 |
| Suture Threading Funnel | 18 |
| Handle | 19 |
| Suture Outlet | 20 |
| Suture | 21 |
| Filament | 22 |
| Skin Opening (Cannula not shown) | 23 |
| Meniscal Tear | 24 |
| Anterior Cruciate Ligament Tear | 25 |
| Knot Pusher | 26 |
| Arthroscope | 27 |

21 Claims, 18 Drawing Sheets

U.S. PATENT DOCUMENTS

| | | | |
|---|---|---|---|
| 5,069,226 | 12/1991 | Yamauchi et al. | 128/772 |
| 5,154,189 | 10/1992 | Oberlander | 128/898 |
| 5,181,919 | 1/1993 | Bergman et al. | 606/144 |
| 5,219,358 | 6/1993 | Bendel et al. | 606/222 |
| 5,222,977 | 6/1993 | Esser | 606/223 |
| 5,250,055 | 10/1993 | Moore et al. | 606/148 |
| 5,282,809 | 2/1994 | Kammerer et al. | 606/148 |
| 5,290,284 | 3/1994 | Adair | 606/37 |
| 5,312,422 | 5/1994 | Trott | 606/144 |
| 5,330,491 | 7/1994 | Walker et al. | 606/148 |
| 5,364,410 | 11/1994 | Failla et al. | 606/148 |
| 5,374,268 | 12/1994 | Sander | 606/72 |
| 5,398,861 | 3/1995 | Green | 227/175 |
| 5,462,560 | 10/1995 | Stevens | 606/144 |
| 5,468,251 | 11/1995 | Buelna | 606/223 |
| 5,474,565 | 12/1995 | Trott | 606/144 |
| 5,499,991 | 3/1996 | Garman et al. | 606/148 |

Retracted Position      Deployed Position

PARTIAL TO FULL THICKNESS SUTURE DEVICE & METHOD FOR ENDOSCOPIC SURGERIES

BACKGROUND OF THE INVENTION

1. Field of the Invention

This invention relates to devices and methods for delivering partial-thickness or full-thickness sutures in tissues endoscopically. This invention also relates to devices and methods used to minimize the strain and stress of shape memory materials.

2. Description of Prior Art

In recent years, much attention has been given to control surgical costs. One of the cost saving approaches is to accelerate the speed of recovery and shorten hospital stays after surgeries. Beyond cost savings, for the comfort and safety of patients, minimally invasive or endoscopic surgeries are becoming more and more popular. The term "endoscopic" used in this invention encompasses arthroscopic, laparoscopic, hysteroscopic and other procedures. Endoscopy is a surgical procedure which allows surgeons to manipulate instruments to view the surgical sites through small incisions in the bodies of patients.

An endoscopic surgery begins with puncturing holes through soft tissue such as skin and muscle. After the holes are made with sharp instruments, hollow cylindrical tubes called cannulas are inserted through the holes of the soft tissue. These cannulas serve as tunnels for the endoscope and surgical instruments reaching into the surgical site.

In order to minimize both the patients' trauma and potential damage to nerves, blood vessels and other tissues, it is clearly desirable to minimize the size and number of holes puncturing the patients. Take meniscal repair in the knee for example, the current arthroscopic procedure requires one hole for the arthroscope, one hole for a needle to deliver a suture and another hole for a suture-retrieving instrument to complete one suture stitch (Arthroscopic Surgery by L. Johnson, M.D.; Knee Surgery by F. Fu, M.D., et al.; Traumatic Disorders of the Knee by J. Siliski, M.D.; and Knee Surgery Current Practice by P. Aichroth, FRCS et al.). A minimum of three holes are made for the arthroscopic repair. In some cases, surgeons also require a distractor, an external fixation device which is screwed in through skin to the bones, spreading the femur from the tibia. This expands the knee joint and makes room to manipulate both the suture and the suture-retrieving instrument. Due to the tightness of joint space, often needles or instrument can accidentally scrape and damage the smooth surface of the joint, which given time, can potentially lead to osteoarthritis years after the surgery.

Arthroscopic and endoscopic suturing are done with a full-thickness technique, where sutures penetrate all the way through a tissue for each stitch. In the case of meniscal repair, the full-thickness suture repair can potentially cause long term problems, including osteoarthritis, from the constant rubbing of a very smooth joint surface to the exposed suture on the surface of the meniscus. Unless the damaged tissues can be lifted, shifted or somehow separated from crowded adjacent tissues, endoscopic procedures usually cannot be performed due to insufficient space for manipulating sutures and instruments. In these cases and others, conventional open surgery using partial-thickness suturing techniques with a curved needle, where the suture enters and loops back out without full-thickness penetration, is pursued for the repair.

Some needles (U.S. Pat. No. 5,474,565 to Trott, 1995; U.S. Pat. No. 5,222,977 to Esser, 1993; U.S. Pat. No. 5,330,491 to Walker et. al.) are designed for endoscopic surgical use. These surgical needles require multiple cannula punctures and cumbersome suture manipulation to complete each stitch.

In summary, the current instruments used in endoscopic procedures have one or more of the following drawbacks or restrictions:

(A) Increased surgical trauma due to multiple puncture wounds needed to accommodate suture manipulation and retrieving instruments.

(B) Increased risk of damaging nerves, blood vessels, joint cartilage or adjacent tissues with multiple punctures and suture manipulation.

(C) Lengthened surgical time.

(D) Restricted by space required around and behind the surgical site.

(E) Limited to full-thickness suture repair.

Another invention, U.S. Pat. No. 5,250,055 to Moore et. al., 1993, proposed a tissue-fastening technique onto bone. Moore's invention requires the drilling of two parallel holes in bone. The holes are then fitted with double barrels. A suture is attached to a non-hollow shape memory hook straightened by one barrel. As the straightened hook is pushed out of the barrel, the shape of the hook resumes and carves a tunnel in the bone reaching the second drilled hole. Another barrel houses suture retrieving tweezers to pull the suture and complete the suture loop inside the bone. The suture is then used to tie down damaged tissues onto bone. This device is not frequently used because of the large holes it makes in the bone and the difficulty of retrieving the suture with the tweezers inside the bone.

Recently, tacks (U.S. Pat. No. 5,398,861 to Green, 1995; U.S. Pat. No. 5,059,206 to Winters, 1991; U.S. Pat. No. 4,895,148 to Bays et. al., 1990) and staples (U.S. Pat. No. 5,374,268 to Sander, 1994; U.S. Pat. No. 5,154,189 to Oberlander et. al., 1992) made out of polymers and metals have been used as permanent implants to hold torn tissues in place. Very few of these devices have the holding strength of sutures. With time, some tacks and staples creep and leave gaps in the supposed closure sites. Some biodegradable tacks and staples do not last long enough for the damaged tissue to heal before disintegrating. Many of these biodegradable implants also have serious biocompatibility problems which cause inflammation and other harmful cellular interactions. For the long lasting polymeric or metal tacks and staples, there is always the nagging potential problem of device migration, which can be devastating, especially into joints and nerves.

SUMMARY OF INVENTION

In this invention, a suture can be guided, delivered, retrieved and tied through one opening in the skin with no additional suture retrieving instrument, for partial-thickness or full-thickness repairs.

The major components of this suturing device comprise of three needles. A hollow suture-delivering needle mounts parallel or near parallel to a hollow suture-retrieving needle, with depth of penetration markings on the outsides of the needles visible to an endoscope. The sharp tips of the needles are the distal ends of the needles. A third, smaller gauged hollow shape memory needle, SMN, made out of material such as nickel-titanium alloy, high carbon steel or polymer, is bent with its shape retained in a small semicircular hook at and near the sharp tip, distal end, of the SMN.

In its retracted position, the sharp hook of the SMN is housed and is partially straightened inside the suture delivering needle. To minimize the strain and stress exerted on the shape memory hook by the inside bore of the suture delivering needle, a strain, stress relief window is opened to the outside of the suture delivering needle, where the back of the hook is partially protruded from inside and exposed at or near the surface of the suture delivering needle. On the opposite side of the strain, stress relief window, a gliding slot with a tapering trough is made at the opening of the suture delivering needle allowing the sharp hook of the SMN to slide in and out of the distal opening of the suture delivering needle.

To deploy the SMN, a hand operated lever connecting to the proximal portion of SMN pushes the hook out through the gliding slot of the suture delivering needle. In a deployed position, the sharp hook extends out of the delivering needle and follows a semi-circular path into a SMN receiving slot in the adjacent suture receiving needle.

To initiate an endoscopic surgical procedure, a skin puncture is made through which a cannula is placed. The repair site is examined with an endoscope, and the ideal placement of the suture is determined. After examination, the endoscope is withdrawn from the cannula then inserted into an equipment inlet and protruded through an equipment outlet of the suture device. Through the cannula, the suture device is guided by the view transmitted by the endoscope to the surgical site. The sharp suture delivering and suture receiving needles are pierced into the previously determined suture placement site. The depth of penetration of both needles are indicated by the penetration markings on the needles, visible to the endoscope. When the ideal depth is reached, the hook of SMN, which is initially set in a retracted position, is deployed from the suture delivering needle into the SMN receiving slot of the suture receiving needle. Since the distal end of the SMN is sharp, it can pierce the tissue as it is deployed enroute to the SMN receiving slot of the suture receiving needle, forming a partial-thickness suturing. On the other hand, if the tissue is initially pierced through by both the suture delivering and suture receiving needles, and the hook of the SMN is deployed outside the tissue, then a full-thickness suturing will be formed.

For ease of suture threading, the endoscope can now be withdrawn from the device. To aid in the suture threading process, a funnel is connected to the proximal opening of the SMN. For surgical operations in which braided sutures are preferred, a long piece of flexible filament is fused and connected, tip to tip, with the braided suture; mono-filament sutures on the other hand can possibly be threaded directly without the aid of the flexible filament. For repairs which required high tensile strength, instead of suture, a wire or cable can be used. Using pushing and twisting motions on the filament, the filament or mono-filament suture is advanced through the suture threading funnel into the inner bore and out of the distal opening of the SMN, then into the distal opening of the suture-receiving needle and out its proximal opening. The suture is now in and around the repair site, with both ends of the suture outside the body of the patient.

For a SMN with a small hook, it can be difficult to push the suture or filament along a small semi-circle path inside the SMN. Instead of following the semi-circle path of a deployed hook, while the hook is partially straightened inside the suture delivering needle, the suture can more easily be advanced until the tip of the suture or filament is pushed near the distal opening of the straightened hook. As the partially straightened hook is deployed resuming the shape of the hook with the suture inside, the tip section of the suture or filament is already around the small semi-circle, the most difficult segment of the suture passing route. The rest of the suture passing can then be easily advanced through the inner bore and out the proximal opening of the suture receiving needle.

Before suture tying, the SMN is retracted back into the suture delivering needle. The filament connecting to the braided suture is cut off. The suture device is withdrawn, leaving the suture in and around the surgical site.

As mentioned earlier, partial or full-thickness suture can be placed depending on whether the SMN was deployed within or outside the surgical tissue. If the deployment was within the tissue, then it will be a partial-thickness suture repair. On the other hand, if the deployment was outside the tissue, then it will be a full-thickness suture repair. In some cases, it is also possible to have a combination of both partial and full-thickness suture repairs.

Slip knots are then tied and delivered with a knot pusher to the surface of the surgical site. Excess suture is cut off with endoscopic scissors to finish a stitch of suture repair. The process is repeated for multiple stitches to fasten tissues endoscopically, with partial-thickness or full-thickness suture repairs selected on a stitch by stitch basis.

Furthermore, the utilization of a SMN to bridge the suture delivering and the suture receiving needles in this invention can also be used to pass suture into bone. For example, two holes can be pre-drilled into cortical bone prior to inserting the suture delivering and receiving needles. Beneath the cortical bone, a much softer and porous trabecular bone can be pierced by the sharp SMN.

This invention has many advantages over tacks and staples. Sutures are being used and have been proven and well accepted as fastening devices in open and some endoscopic surgeries for a long time without significant adverse effects. On the other hand, use of tacks and staples as implants always bear concerns over their biocompatibilities, rates of resorption and creeping, and implant migrations. In this invention, well-placed sutures are the only implant materials, and using proven knot tying techniques mastered by all well trained endoscopic surgeons ensure a tight and trouble-free partial-thickness or full-thickness endoscopic suture repair.

In summary, this invention has the following possible benefits over the current instruments used in endoscopic suture repair:

(A) Single puncture wound needed to place, manipulate and retrieve a suture.

(B) Minimal risk of damaging nerves, blood vessels, joint cartilage or adjacent tissues with single puncture and minimal suture manipulation.

(C) Shortened surgical time.

(D) Minimal space required around and behind the surgical site.

(E) Capable in accomplishing both full-thickness as well as partial-thickness suture repair.

BRIEF DETAILED DESCRIPTION OF THE DRAWINGS

Figure 1A:
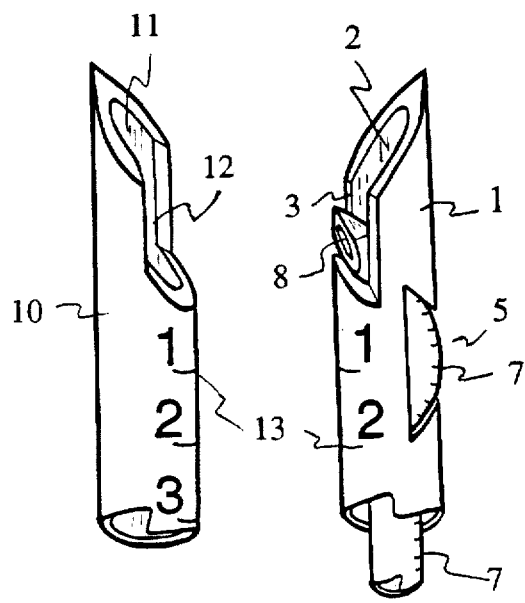
FIG. 1A depicts a suture delivering needle, SDN, 1 on the right and a suture receiving needle, SRN, 10 on the left with a retracted shape memory needle, SMN, 7 mostly housed inside the bore of SDN 1; a substantial portion of a sharp hook of the SMN 7 occupies a strain, stress relief window, SRW, 5 on the SDN 1.
Figure 1B:
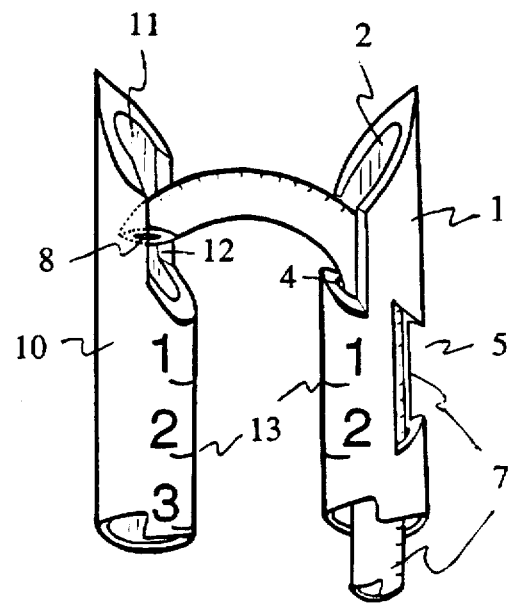
FIG. 1B depicts the same needles as FIG. 1A, but the SMN 7 is in a deployed position bridging the gap between SDN 1 and SRN 10 with the SMN 7 extending into a receiving slot 12.
Figure 1C:
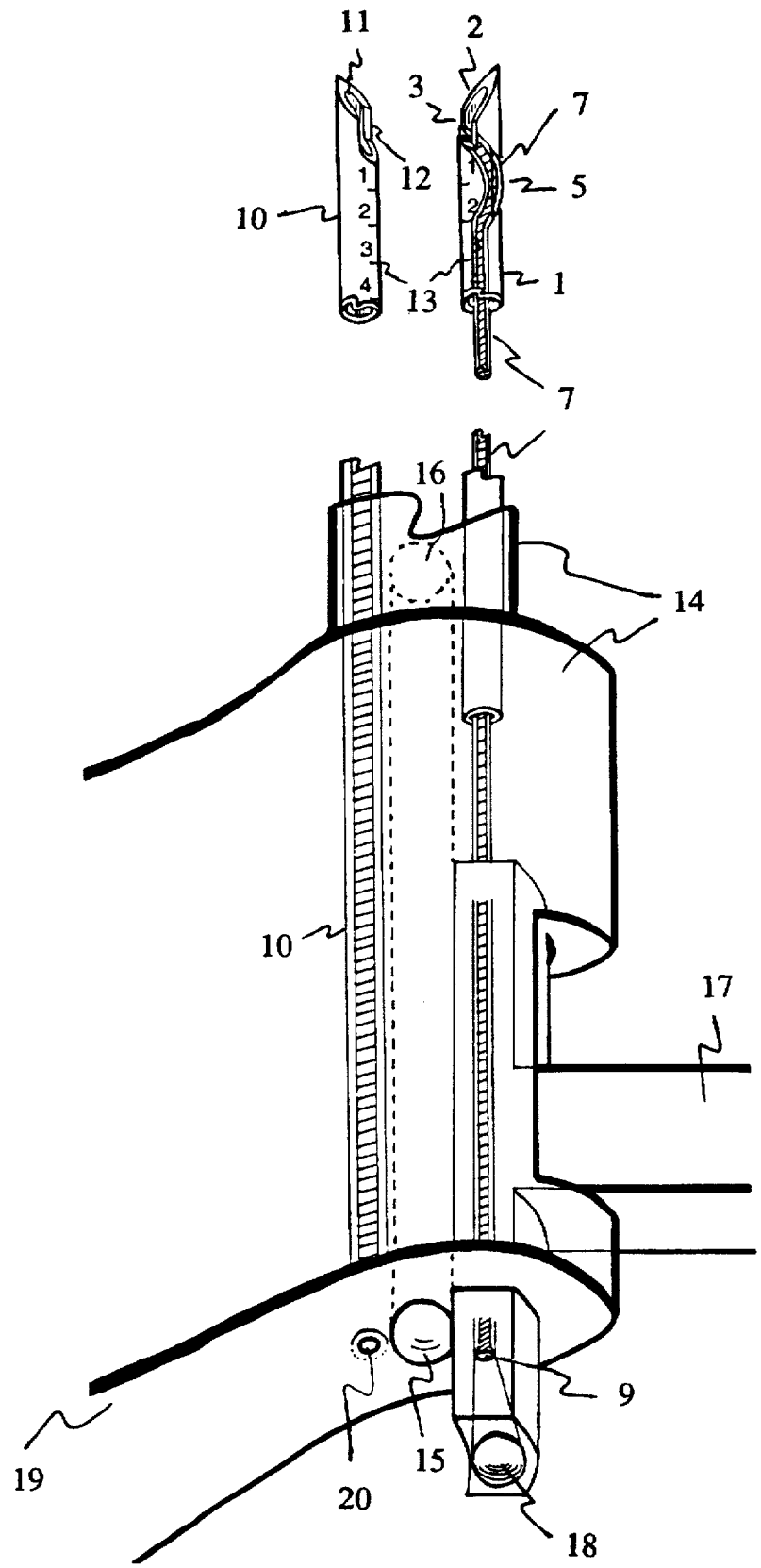

FIG. 1C depicts an internal construction of a suture device with the SMN 7 in a retracted position: a suture threading funnel 18 connecting to a SMN proximal beveled opening 9; an operating lever 17; an equipment inlet 15 and a suture outlet 20.

Figure 2:
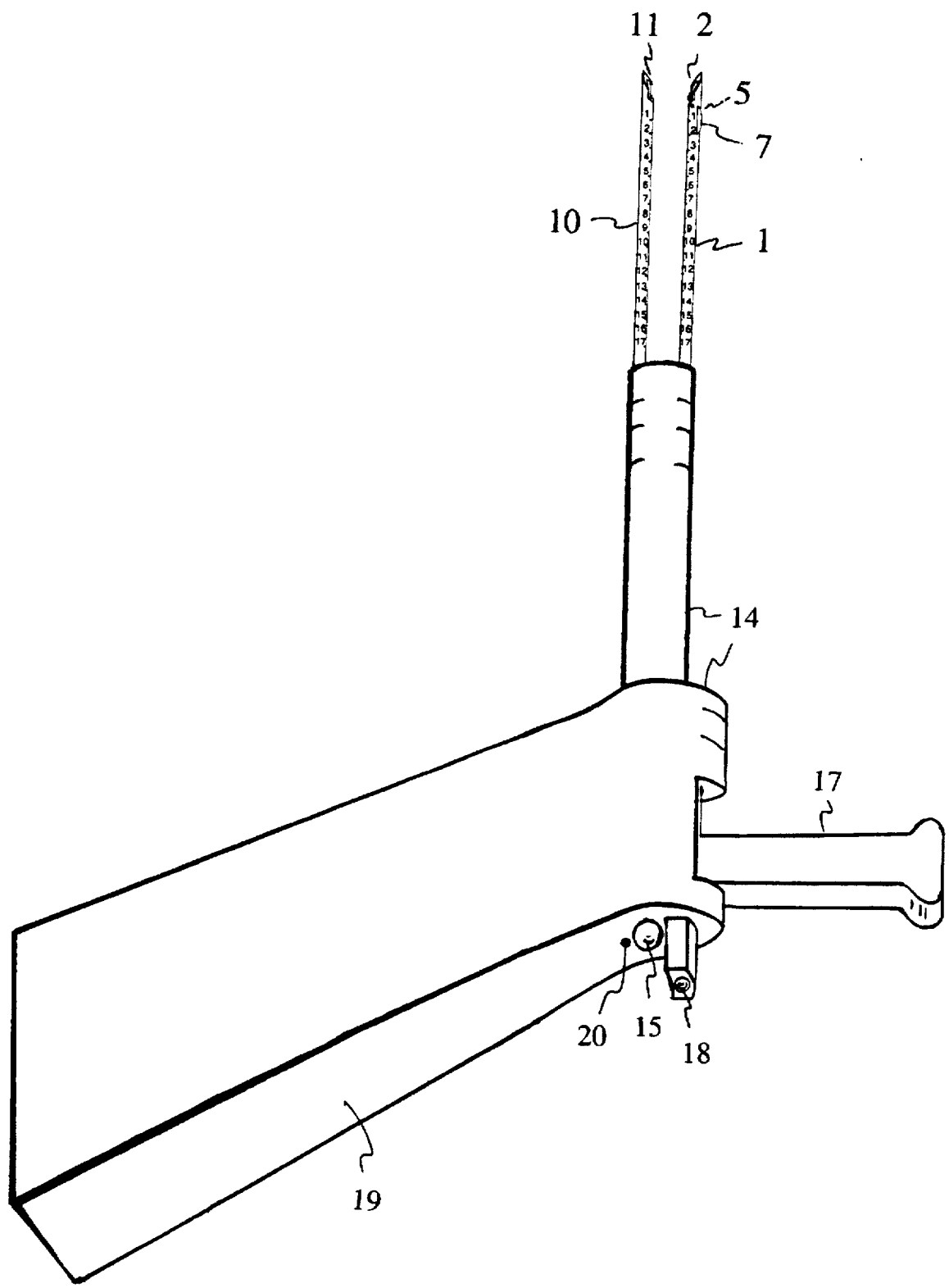

FIG. 2 depicts side and back views of the suture device with the SMN 7 in a retracted position, with the hook housed inside the SDN 1 on the right.

Figure 3:
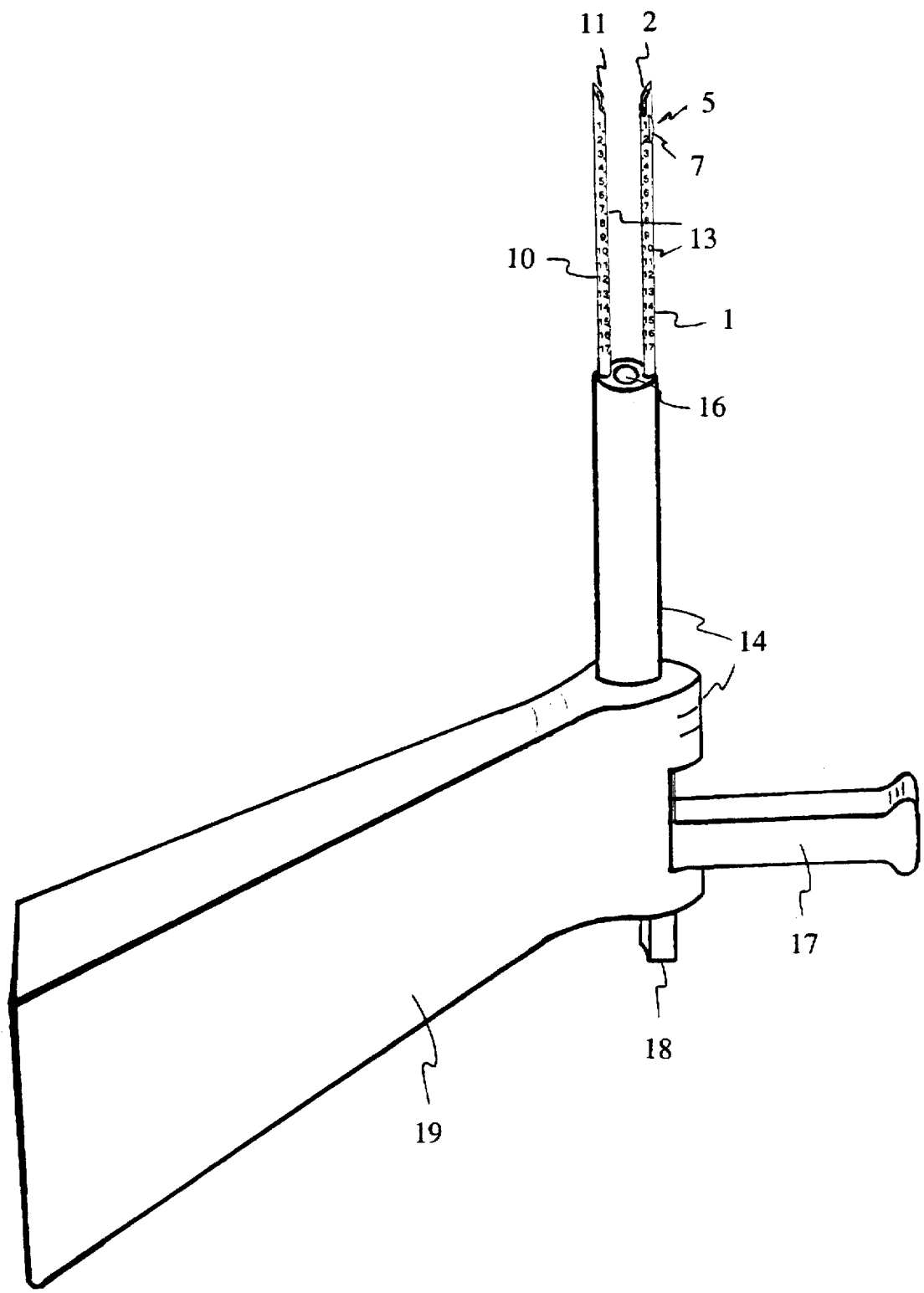

FIG. 3 depicts side and front views of the suture device with the SMN 7 retracted as indicated in FIG. 2. Penetration markers 13 on both the SDN 1 and SRN 10 are visible by an endoscope (not shown) extending from an equipment outlet 16 between the needles.

Figure 4:
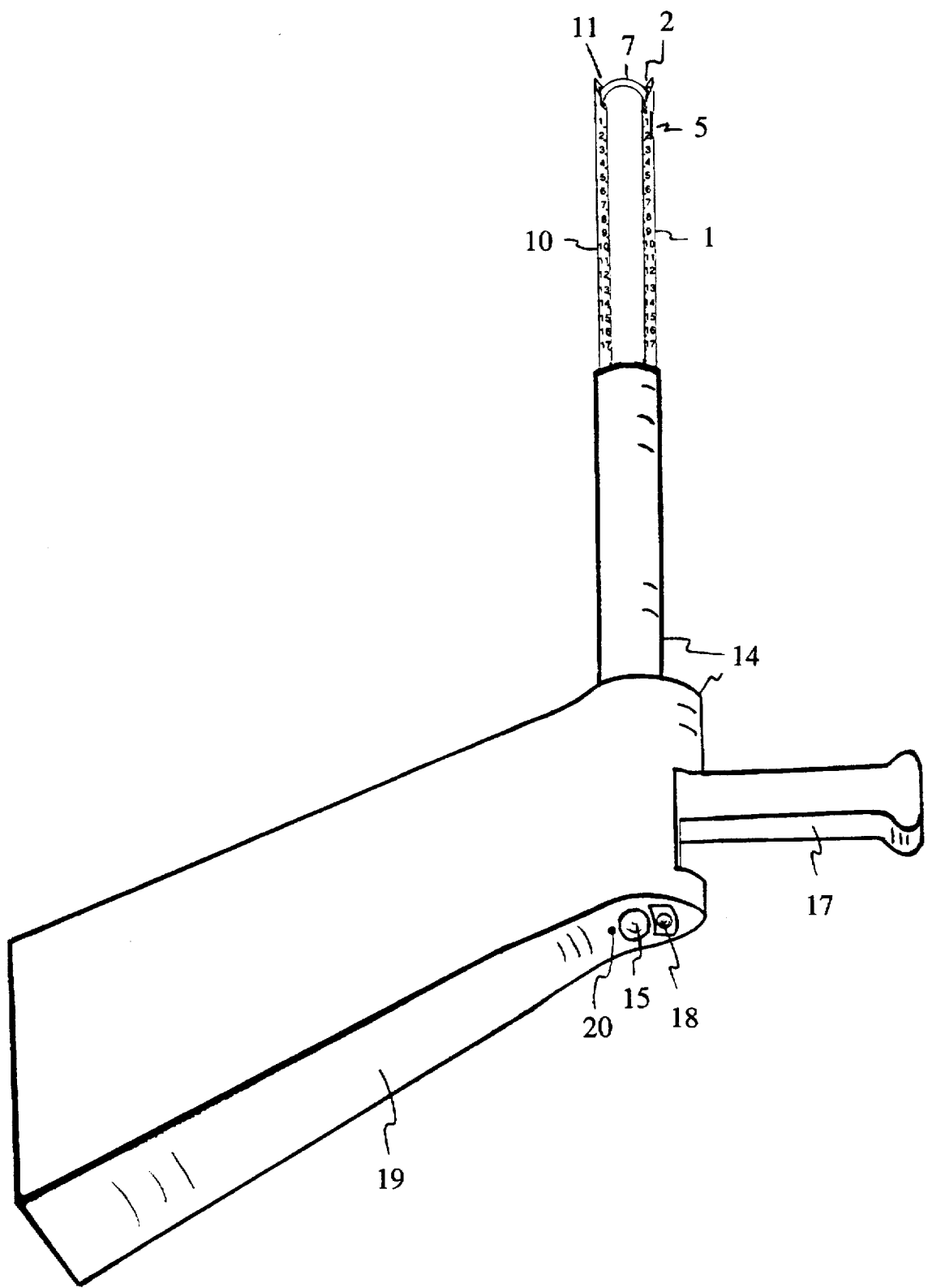

FIG. 4 depicts the same views as FIG. 2 with a deployed SMN 7 into the adjacent SRN 10.

Figures 5A, 5B:
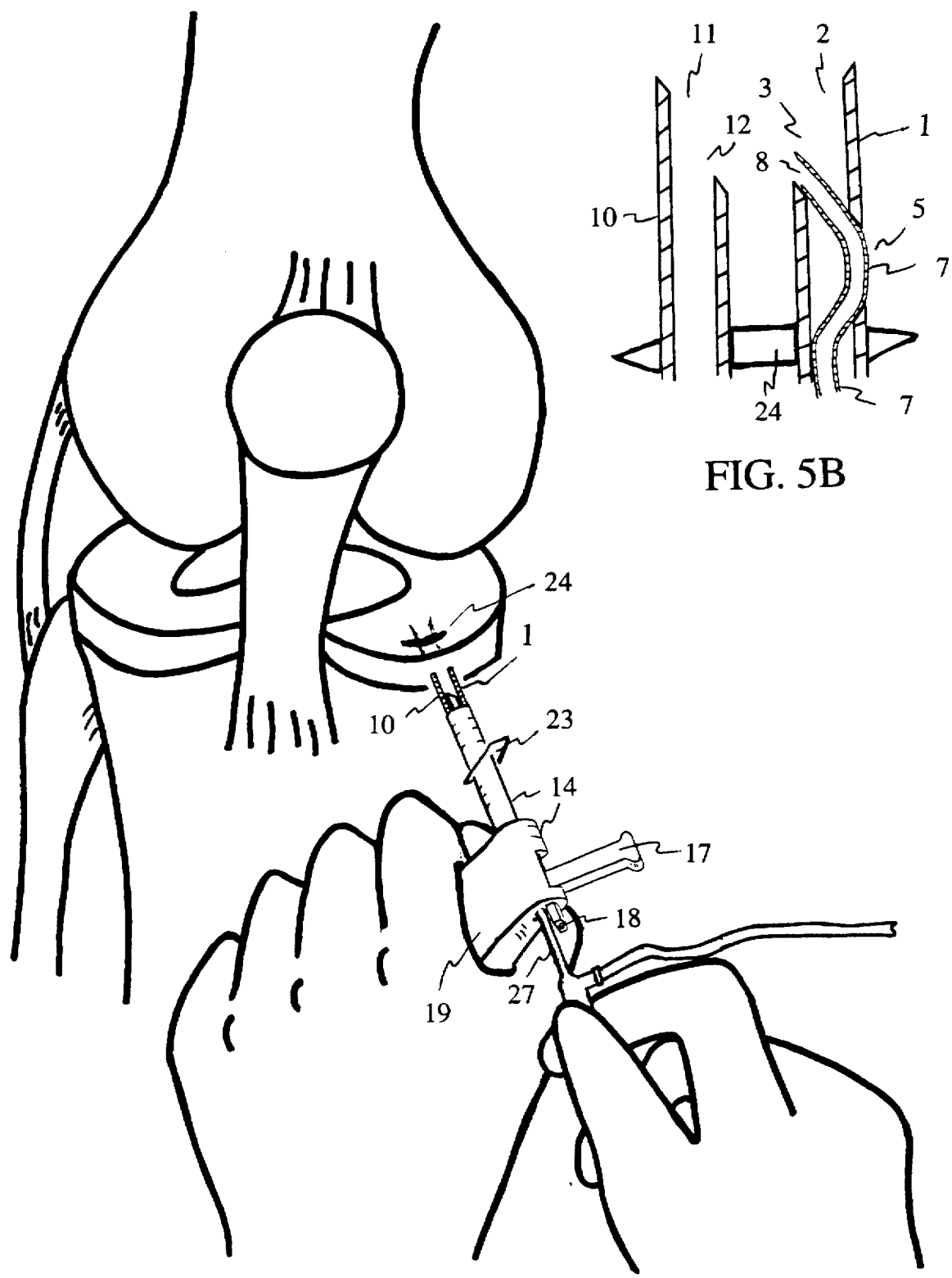

FIG. 5A depicts an arthroscope 27 guiding the penetration of the suture device through a small skin opening 23 (cannula not shown) into a torn meniscus 24 for a partial-thickness suture repair.

FIG. 5B depicts an enlarged and longitudinal mid-section of the needles, with the SMN 7 in a retracted position.

Figures 6A, 6B:
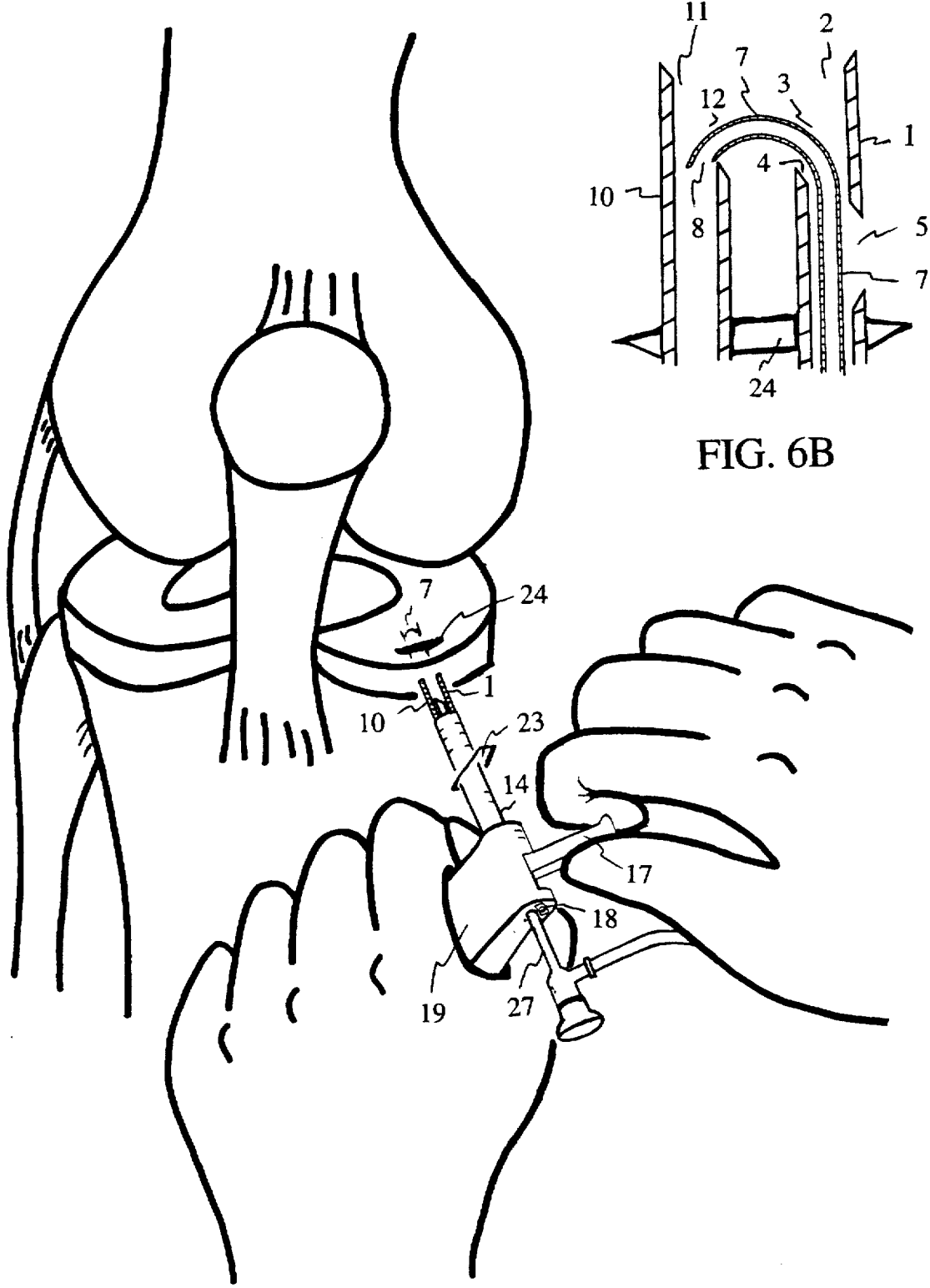

FIG. 6A depicts the deployment of the SMN 7 in a torn meniscus 24. (The arthroscope removal following this deployment is not shown).

FIG. 6B depicts an enlarged and longitudinal mid-section of the needles with the SMN 7 in a deployed position bridging between SDN distal opening 2 and SRN distal opening 11.

Figures 7A, 7B:
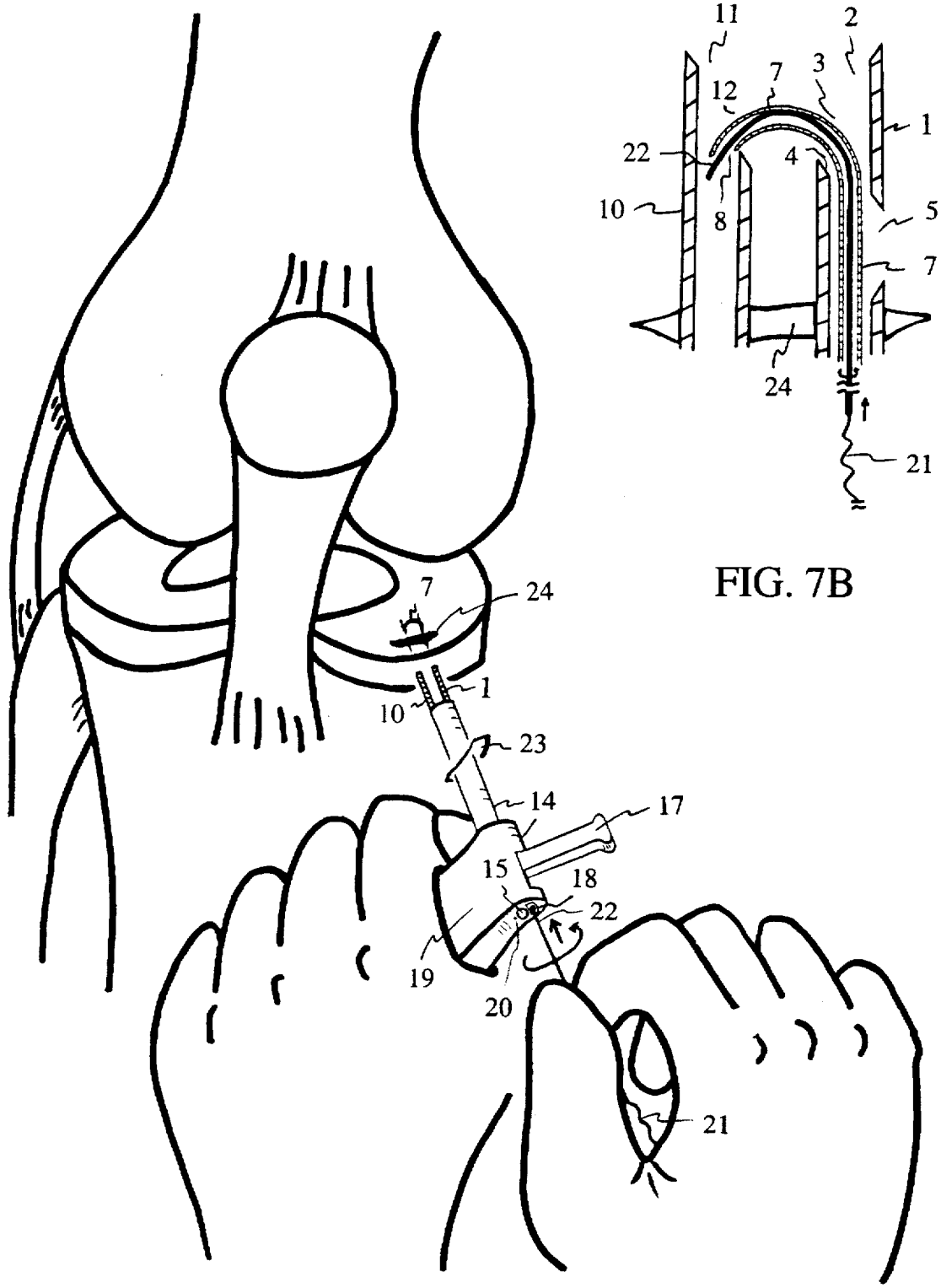

FIG. 7A depicts a suture threading process into the device through a suture threading funnel 18, into a SMN proximal beveled opening 9 (see FIG. 1C), using the pushing and twisting motion on a filament 22 connecting to a soft suture 21.

FIG. 7B depicts an enlarged and longitudinal mid-section of the needles with the filament 22 connected to the suture 21 passing through the SMN 7 from the SDN 1 into a receiving slot 12 opened to the SRN distal opening 11.

Figures 8A, 8B:
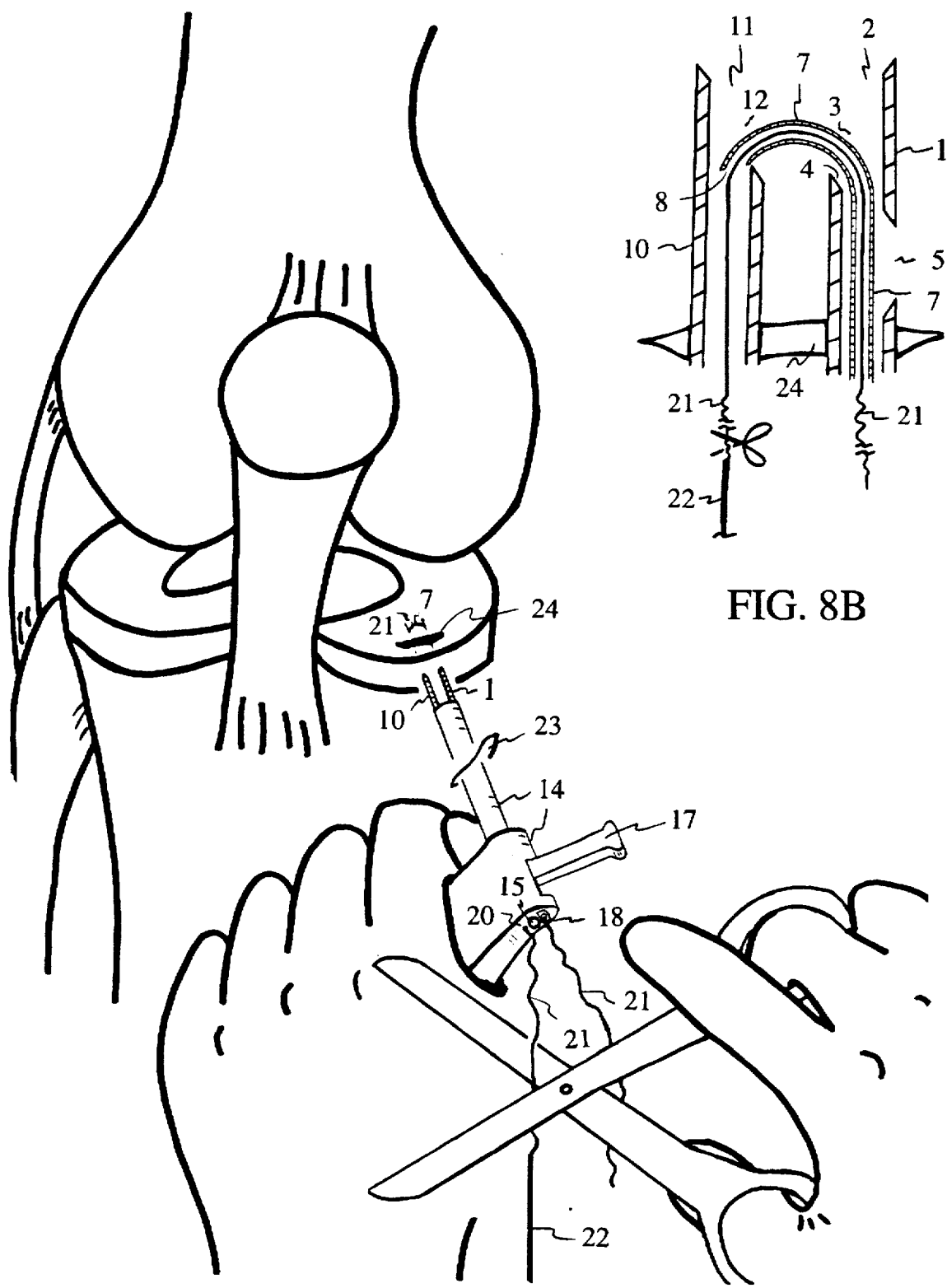

FIG. 8A depicts the cutting of the filament 22, after leading the suture 21 in, through and around the meniscal tear 24, and coming out of a suture outlet 20 of the device.

FIG. 8B depicts an enlarged and longitudinal mid-section of the needles with the suture 21 looped around the meniscal tear 24 from the SDN 1 to the SRN 10 bridged by the SMN 7.

Figures 9A, 9B:
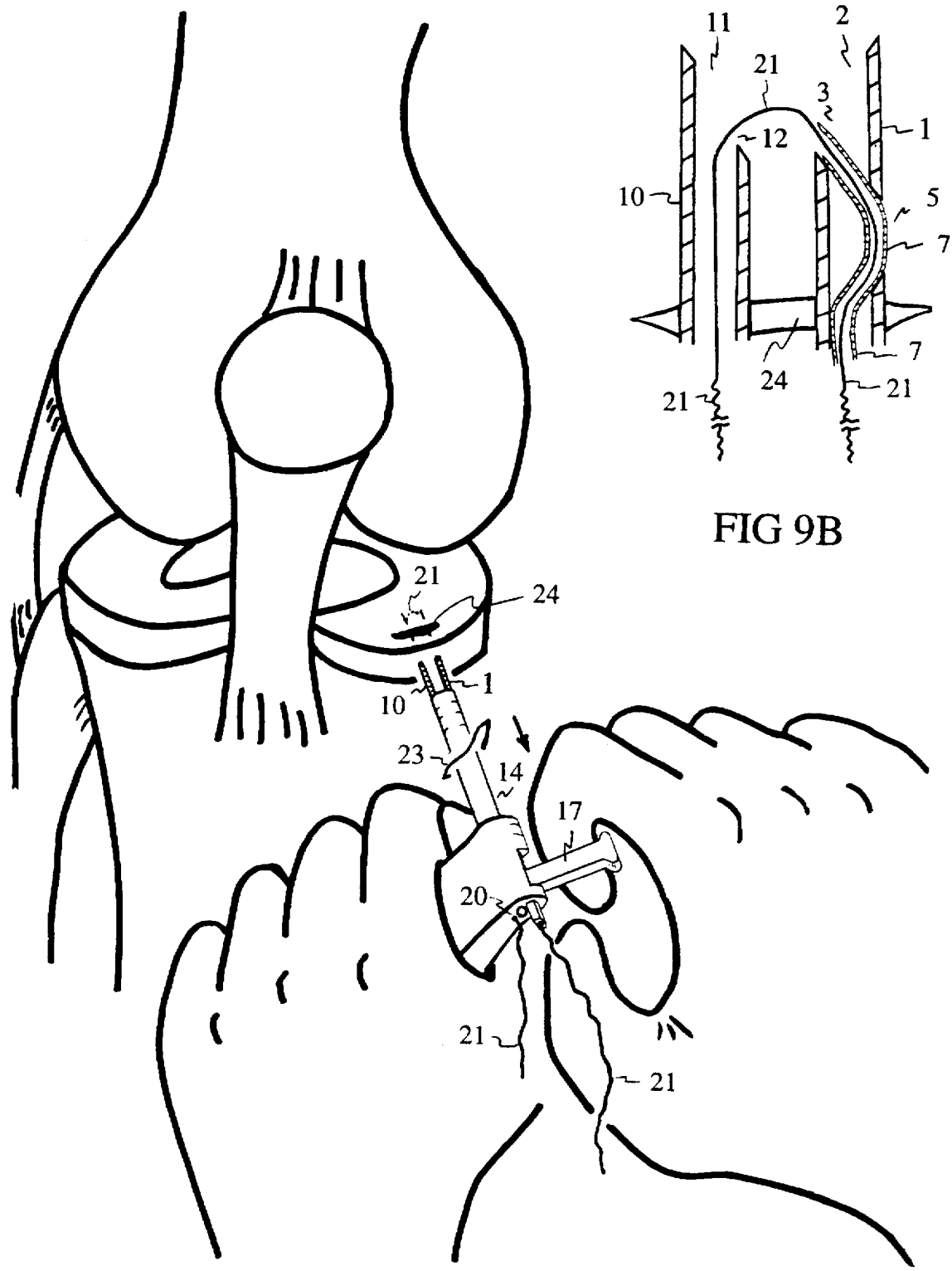

FIG. 9A depicts a process of retracting the SMN 7, leaving only the suture 21 joining between the SDN 1 and the SRN 10.

FIG. 9B depicts an enlarged and longitudinal mid-section of the needles with a retracted SMN 7, leaving only the suture 21 joining between the SDN distal opening 2 and the SRN distal opening 11.

Figures 10A, 10B:
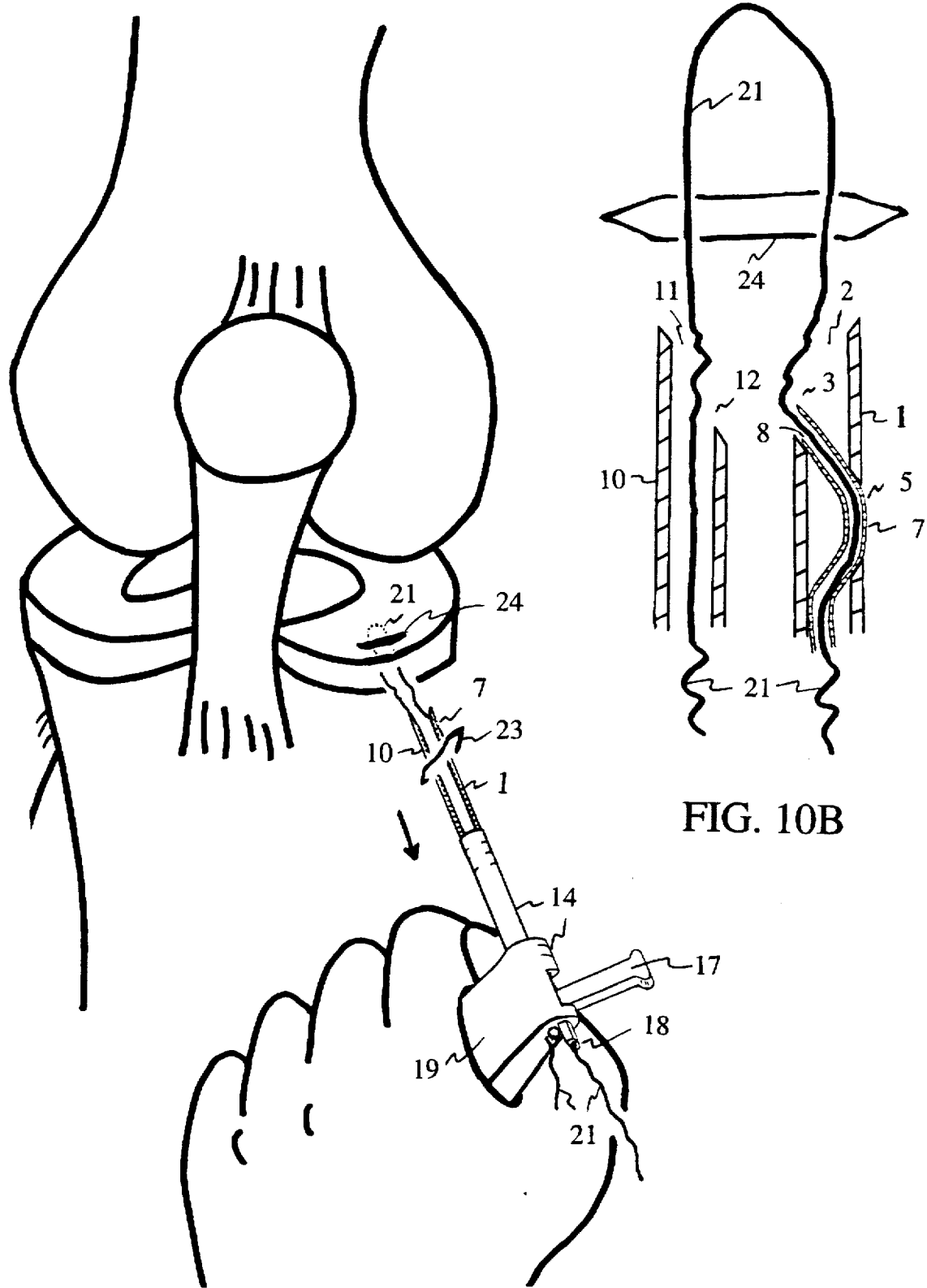

FIG. 10A depicts a process of withdrawing the suture device with the suture 21 remaining at the repair site.

FIG. 10B depicts an enlarged and longitudinal mid-section of the withdrawn needles with the suture 21 remaining at the repair site.

Figure 11B:
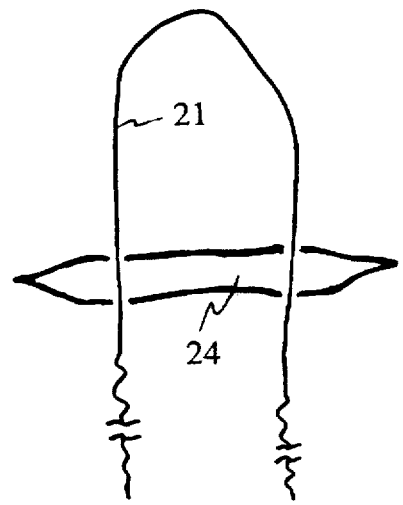
Figure 11A:
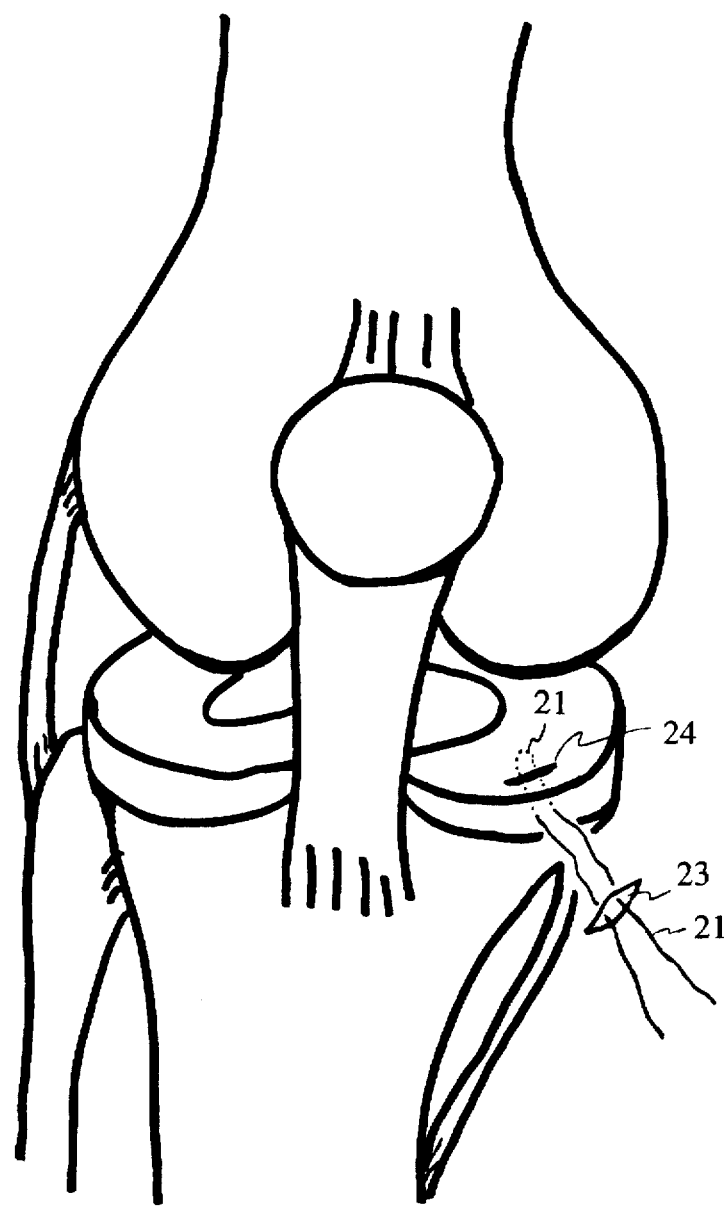

FIG. 11A depicts the partial-thickness placement of the suture 21 in the meniscal tear 24 with the suture device withdrawn.

FIG. 11B depicts an enlarged view of the suture 21 in and around the meniscal tear 24.

Figure 12:
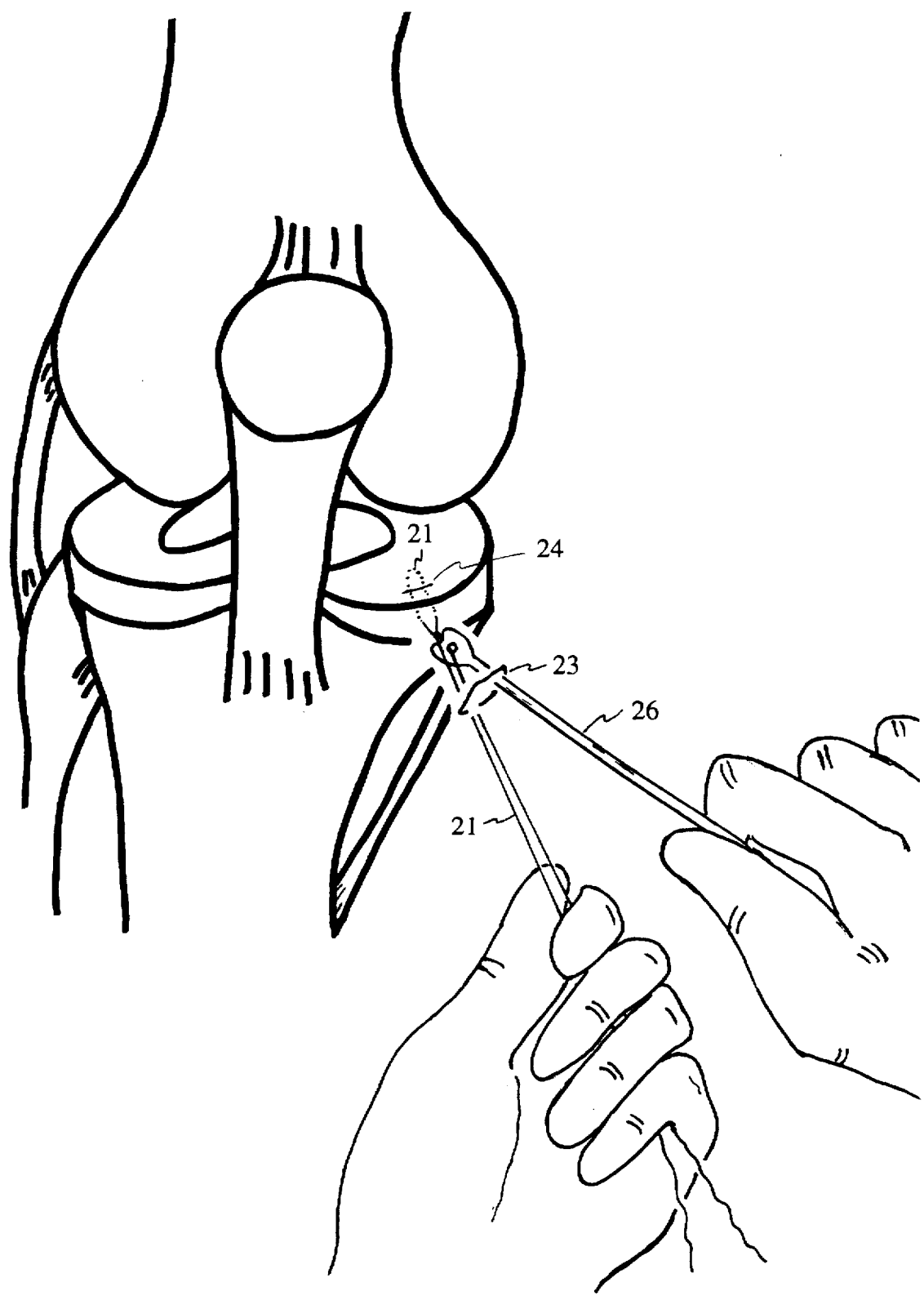

FIG. 12 depicts a suture tying process using a knot pusher 26 tying a slip knot to fasten the torn portion of meniscus 24.

Figure 13:
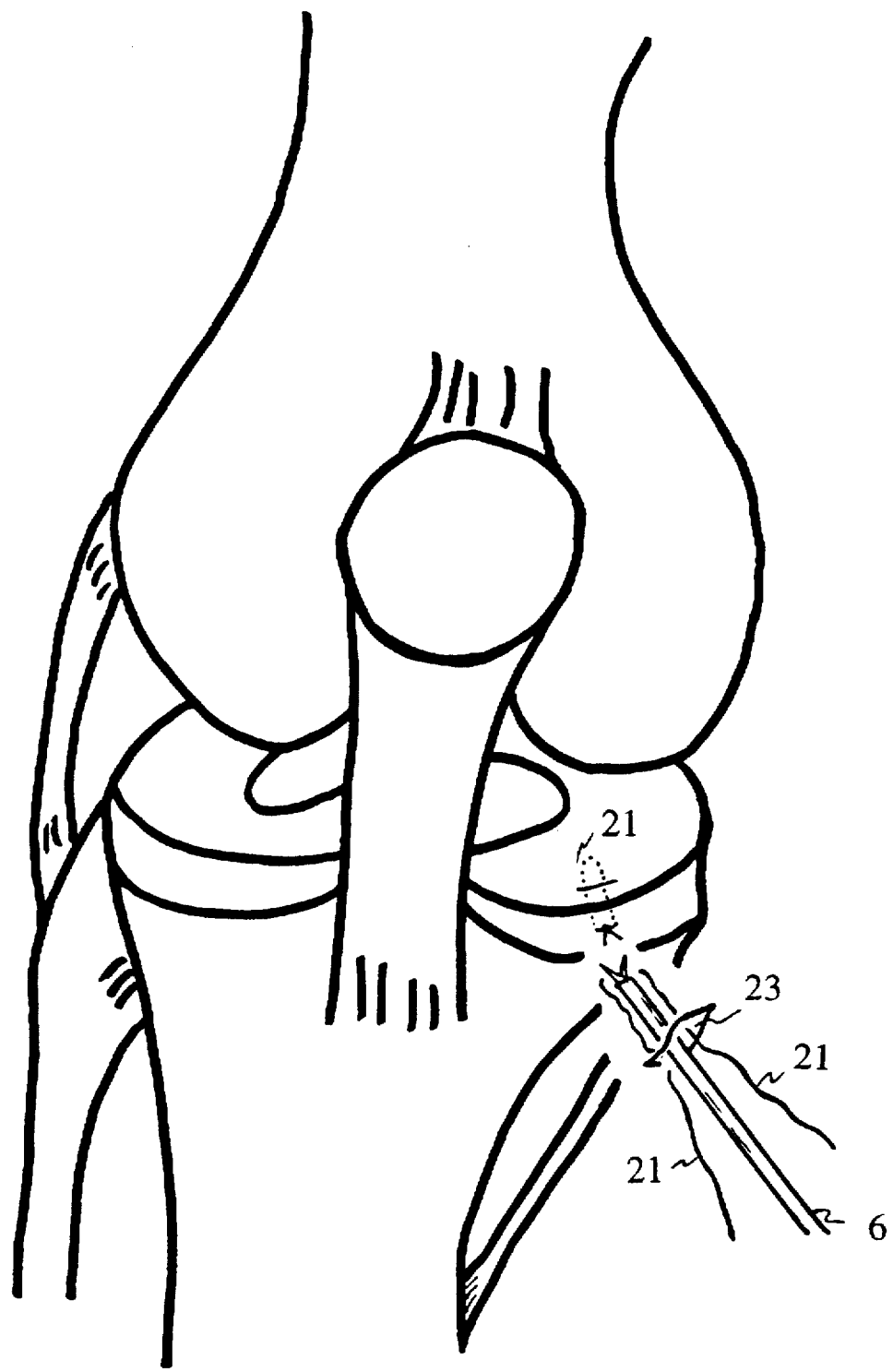

FIG. 13 depicts a partial-thickness suture repair of a meniscal tear. Excess suture 21 is cut off with endoscopic scissors 6.

Figure 14:
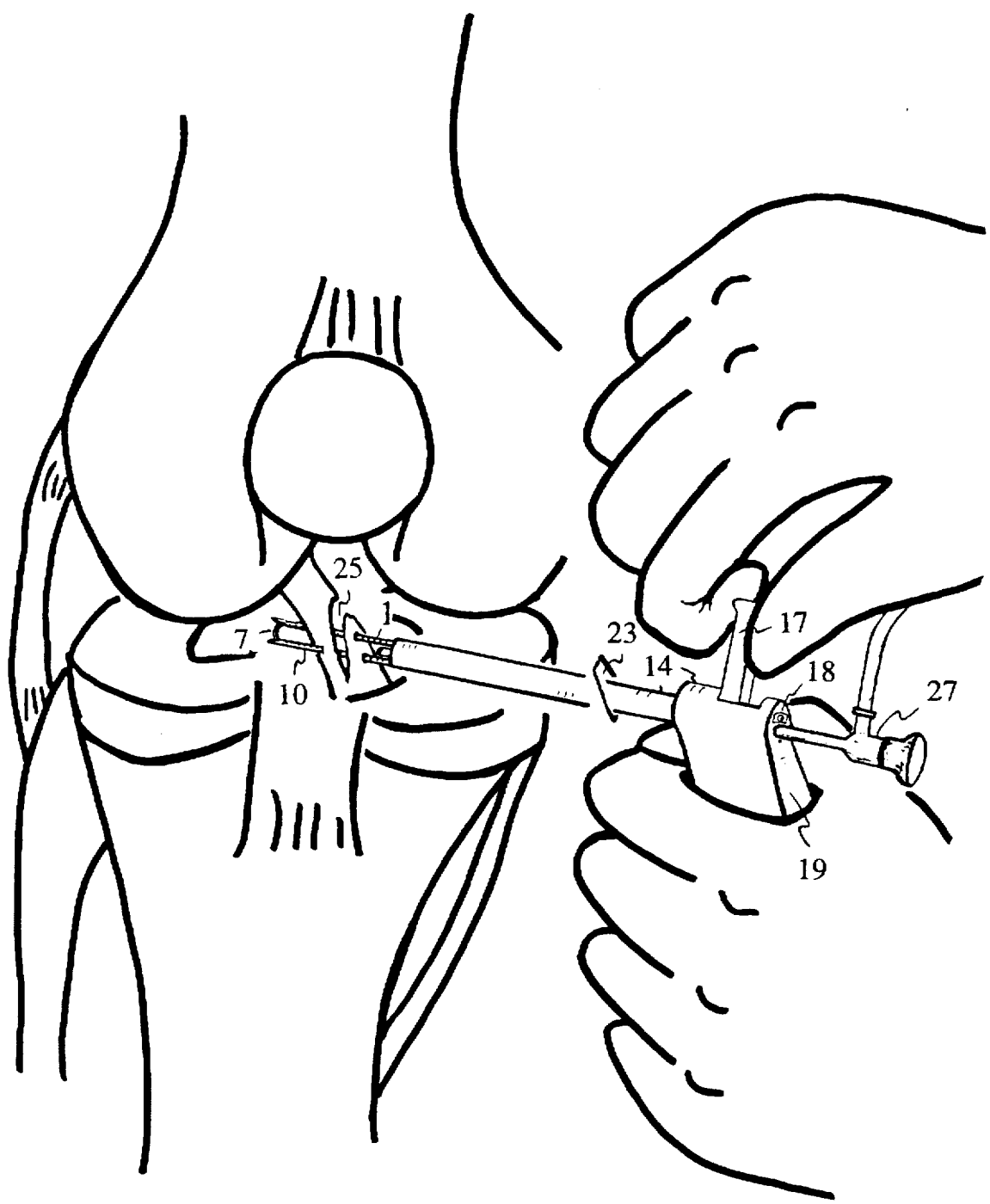

FIG. 14 depicts an arthroscopically guided full-thickness suture repair of a partially torn anterior cruciate ligament 25, with the SMN 7 in a deployed position.

Figure 15:
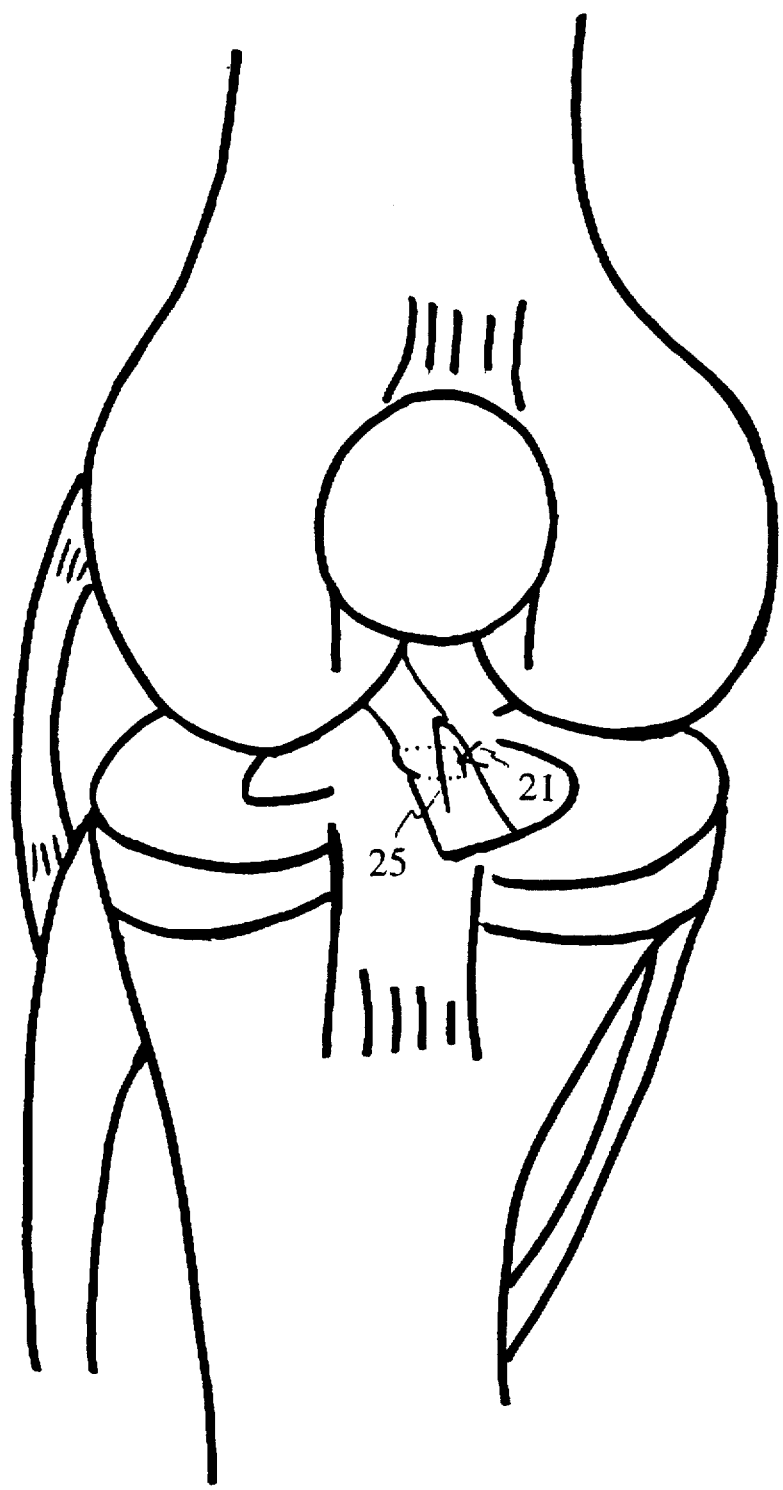

FIG. 15 depicts a full-thickness suture repair of a torn anterior cruciate ligament 25.

Figure 16:
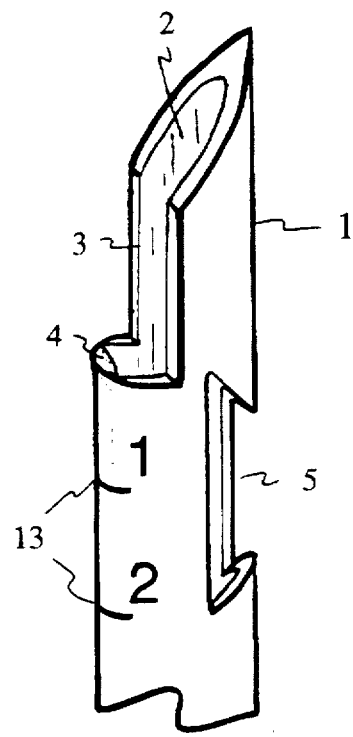

FIG. 16 depicts a strain, stress relief window, SRW, 5, a gliding slot 3 and a trough 4 of the SDN 1 for housing and deploying the SMN 7 (not shown).

Figure 17A:
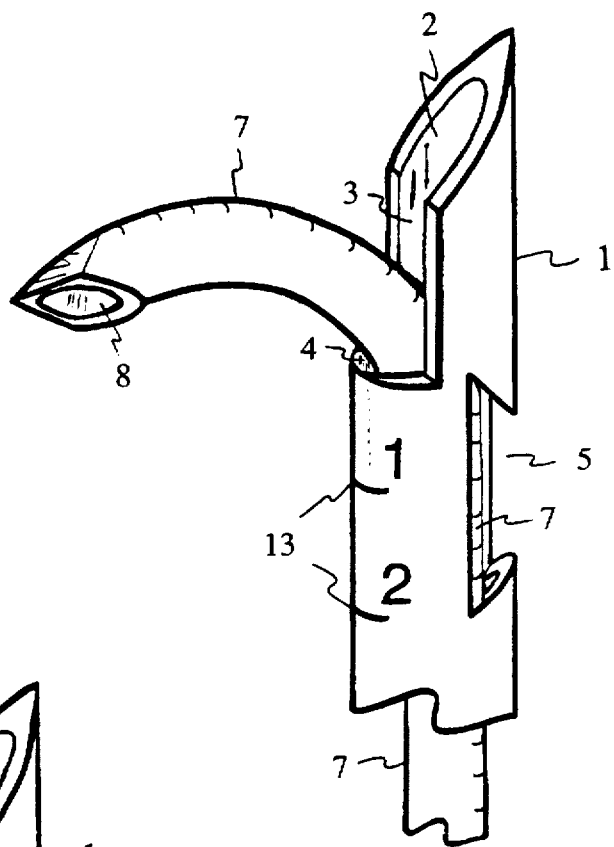

FIG. 17A depicts a preferred tip sharpening of a SMN distal opening 8 indicated in a deployed position and the preferred angle opening of SRW 5.

Figure 17B:
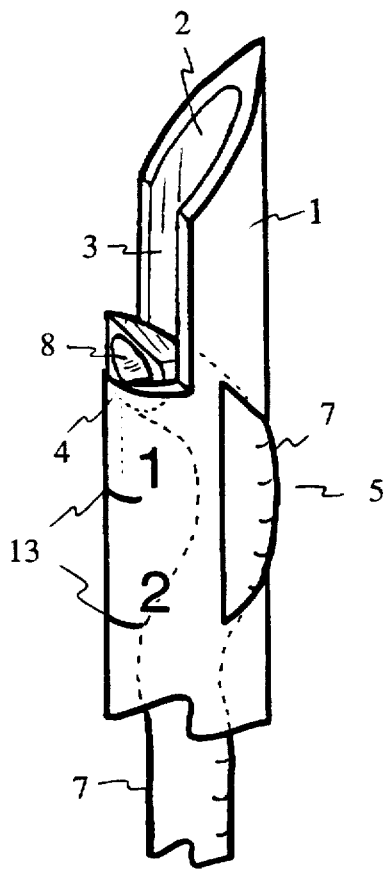

FIG. 17B depicts, in retracted position, the locations of the SMN distal opening 8 resting on the trough 4 slightly outside the inner bore of SDN 1; and the hook portion of SMN 7 is partially straightened inside the SDN 1 and partially occupying the SRW 5.

Figure 18A:
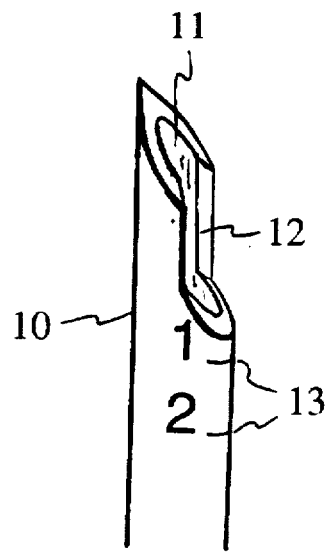

FIG. 18A depicts a preferred lateral-cut angle of a receiving slot 12 on the SRN 10.

Figure 18B:
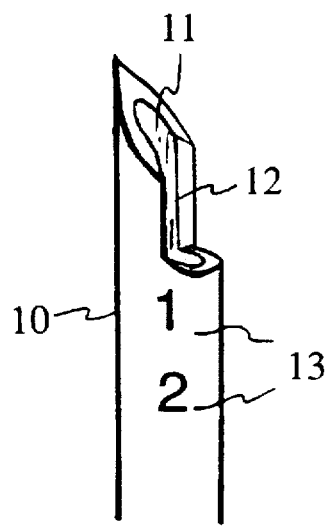

FIG. 18B depicts a right-angle lateral-cut of the receiving slot 12 on the SRN 10.

Figure 18C:
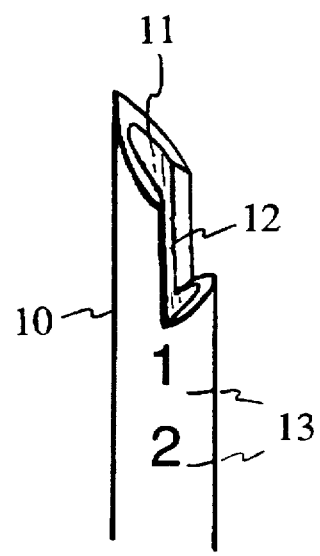

FIG. 18C depicts an acute-angle lateral-cut of the receiving slot 12 on the SRN 10.

DESCRIPTION OF THE PREFERRED EMBODIMENT

The word "needle" is used to describe a needle with tissue puncturing capability, as well as a lumen or an inside bore allowing sutures to pass through. Stainless steel is the preferred material for the suture delivering needle, SDN, 1 and the suture receiving needle, SRN, 10. The shape memory needle, SMN, 7 on the other hand, is best made of nickel titanium alloy or other shape memory alloys sharpened on the inner circumference of the bend, as depicted in FIG. 17A. The preferred materials to use for the handle 19, body 14 and the shape memory needle operating lever 17 are metal or polymer tolerant to multi-sterilization cycles of autoclave, gamma-irradiation, electron-beam irradiation or ethylene oxide.

The suture 21 material can be natural, synthetic, bioabsorbable, non-absorbable, braided, monofilament or metallic. The suture 21 can also be incorporated with blood clot residues, cells, growth factors, tissue healing factors, nutrients, minerals, antibiotics, adhesives, lubricants or other substance.

The preferred material for the filament 22 is a flexible and pushable monofilament polymer tolerant to sterilization methods, such as autoclave, gamma-irradiation, electron-beam irradiation or ethylene oxide. The preferred connection between the filament 22 and the suture 21 is tip to tip fused by heat, light, ultrasound or adhesives. The outer diameters of both filament 22 and suture 21 are preferred to be smaller than the inner diameter of the SMN 7.

All known shape memory materials can lose or partially lose their shape memory with excessive strain, stress or heat upon the materials. To minimize the mechanical strain on the SMN 7 inside the SDN 1, a strain, stress relief window, SRW 5, is opened at the side of the SDN 1, indicated in FIGS. 16, 17A and 17B. The lateral sectional cut of the SRW 5 is preferred at angles to taper the curvature of the bent portion of SMN 7 as indicated in FIG. 17B. In addition to providing strain and stress relief for shape memory materials, such as the SMN 7, the SRW 5 also provides the directional guidance for the deployment of the materials. In this invention, directional guidance of the SMN 7 is predetermined specifically for bridging the gap between the SDN 1 and SRN 10.

As indicated in FIGS. 16, 17A and 17B, the SRW 5 is fully penetrated or opened from the inside bore to outside wall of the SDN 1. Although possibly less effective in relieving the strain and stress and in directing the path of deployment of a shape memory element, another design of the SRW 5 can be an elongated indentation carved from the inside of the bore but not fully opened to the outside wall of the SDN 1.

The gliding slot 3 and the trough 4, indicated in FIG. 16 are other devices in this invention used to reduce the strain and stress of shape memory material, such as the SMN 7. The trough 4 is carved at the inside bore of the SDN 1, tapering distally to the outer edge of the gliding slot 3. The angle of tapering provides a smooth gliding surface for the preferred sharpened angle of SMN 7 depicted in FIGS. 17A and 17B. The tapering trough 4 and the gliding slot 3 provides four possible major benefits: (1) to minimize grinding and dulling of the sharpened tip of SMN 7, (2) to allow the sharpened tip of the SMN 7 in retracted position to house outside the bore of the SDN 1 thereby further minimizing the strain on the SMN 7, (3) to lighten the forces required to deploy the SMN 7, and (4) to orient the direction of deployment of the SMN 7. Both the gliding slot 3 and SRW 5 are essential to providing the directional guidance during the deployment of the shape memory element, in this invention the SMN 7. The direction of deployment is crucial for proper insertion of the SMN 7 into the receiving slot 12 of the SRN 10.

To ensure the proper insertion of the SMN 7 into the receiving slot 12, the preferred angle of longitudinal opening of the receiving slot 12 is depicted in FIGS. 18A, 18B and 18C. During the initial tissue piercing with the SRN 10 along with the SDN 1, the lateral-cut angle of the receiving slot 12 depicted in FIG. 18A is preferred over the angles depicted in FIGS. 18B and 18C to avoid tissue snagging and possible closure of the SMN receiving slot 12.

In case closure of the SRN distal opening 11 results from tissue entrapment during tissue piercing, a wire can be inserted into the suture outlet 20 and passed down the bore of the SRN 10 to clear the closure. Similarly, a wire can also be used to clear a closure of the SMN 7 prior to passing the filament 22 and suture 21 through the SMN.

During surgeries, the SDN 1 and the SRN 10 can mistakenly be twisted by surgeons, causing the SMN 7 to mis-entering into the receiving slot 12. To minimize the twisting, a body 14 is used to fix both needles stationary and to shorten the twistable length of the exposed SDN 1 and SRN 10.

The suture threading process can be facilitated by a suture threading funnel 18 leading into a smaller proximal beveled bore 9 of SMN, as depicted in FIG. 1C.

It should be clear to one skilled in the art that the current embodiment and surgical sites are not the only use for which the invention may be used. Different materials for the needles, body, handle, lever, suture, filament and other components can be used. The use of this invention is also foreseen in other surgical operations to repair various tissues, such as tendon, ligament, muscle, cartilage, skin, bone, organ, tissue grafting and others.

What I claim is:

1. A suture device comprising:

(a) a body having a proximal end, a distal end, and plurality of holes in substantially parallel alignment running from said proximal end to said distal end;

(b) a handle located substantially near said proximal end of said body;

(c) a plurality of needles fixed longitudinally through said plurality of holes and extending out of said body, said plurality of needles having proximal openings, distal tips, distal openings, inside bores, and said distal tips spaced apart by gaps;

(d) said plurality of needles possess a first needle and a second needle;

(e) a shape memory needle longitudinally and slidably housed in said first needle, said shape memory needle having an inside bore, a proximal opening, a distal opening, a distal tip, a hook substantially near said distal opening, and a suture threading means connected to said proximal opening;

(f) an operating means to slide said shape memory needle along said first needle;

(g) said shape memory needle having a retracted position, wherein said hook is substantially housed in said first needle;

(h) said shape memory needle having a deployed position, wherein said distal opening of said hook is substantially inserted into said distal opening of said second needle; and (i) a suture passing from said suture threading means, into said proximal opening and out of said distal opening of said shape memory needle; then into said distal opening of said second needle and exiting through said proximal opening of said second needle.

2. A suture device as recited in claim 1, wherein said body is curved.

3. A suture device as recited in claim 1, wherein said first needle further comprising:

(a) a strain, stress relief window fitting to said hook;

(b) a gliding slot opened to said distal opening;

(c) a trough carved from said inside bore; and (d) penetration markers.

4. A suture device as recited in claim 3, wherein said strain, stress relief window opens from said inside bore to outside wall of said first needle.

5. A suture device as recited in claim 3, wherein said strain, stress relief window opens from said inside bore but does not penetrate outside wall of said first needle.

6. A suture device as recited in claim 1, wherein said second needle further comprising:

(a) a receiving slot opened to said distal opening of said second needle;

(b) said proximal opening opened to outside of said proximal end of said body; and (c) penetration markers.

7. A suture device as recited in claim 1, wherein said shape memory needle further comprising:

(a) a sharp distal tip and a proximal beveled opening; and (b) said hook located substantially near said sharp distal tip.

8. A suture device as recited in claim 7, wherein said shape memory needle is comprised of any material having the characteristics of being shapable under a non-operating condition and resiliently retaining the shape after substantially straightened in an operating condition.

9. A suture device as recited in claim 1, wherein said suture threading means is a funnel.

10. A suture device as recited in claim 1, wherein said operating means is a lever.

11. A suture device as recited in claim 1, wherein said suture further comprises a flexible and pushable filament.

12. A suture device as recited in claim 1, wherein said suture further comprises a substance.

13. A suture device as recited in claim 1, wherein said suture is a wire.

14. A suture device as recited in claim 1, wherein said suture is a cable.

15. A suture device as recited in claim 1, wherein said plurality of needles are curved.

16. A suture device as recited in claim 1, wherein said plurality of entries and outlets are equipment inlets and outlets.

17. A method of endoscopically suturing tissue using said suture device as recited in claim 1 comprises the steps of:
   (a) placing a cannula substantially close to a site of surgical operation;
   (b) setting said shape memory needle in said retracted position;
   (c) inserting an endoscope into an equipment inlet and extending out an equipment outlet;
   (d) inserting said suture device with said endoscope into said cannula;
   (e) guiding by said endoscope, piercing tissue to be sutured with at least one, preferring both said first and second needles;
   (f) threading said suture through said suture threading means into said proximal opening of said shape memory needle;
   (g) passing said suture longitudinally along said inside bore to said distal opening of said shape memory needle;
   (h) deploying said hook of said shape memory needle into a receiving slot of said second needle;
   (i) continue passing said suture through said receiving slot into said inner bore of second needle;
   (j) retrieving said suture from said proximal opening of said second needle outside said suture device;
   (k) retracting said hook, leaving said suture between said distal openings of said first needle and said second needle;
   (l) withdrawing said endoscope from said equipment inlet;
   (m) withdrawing said suture device from said site of surgical operation, leaving said suture in said tissue;
   (n) tying and delivering slip knot to said tissue;
   (o) cutting off excess suture; and
   (p) repeating all of the steps a plurality of times until said tissue is fastened.

18. A method of endoscopically suturing tissue using said suture device as recited in claim 1 comprises the steps of:
   (a) placing a cannula substantially close to a site of surgical operation;
   (b) setting said shape memory needle in said retracted position;
   (c) inserting an endoscope into an equipment inlet and extending out an equipment outlet;
   (d) inserting said suture device with said endoscope into said cannula;
   (e) guiding by said endoscope, piercing tissue to be sutured with at least one, preferring both said first and second needles;
   (f) deploying said hook of said shape memory needle into a receiving slot of said second needle;
   (g) retrieving said endoscope from said equipment inlet;
   (h) threading said suture through said suture threading means into said proximal opening of said shape memory needle;
   (i) passing said suture longitudinally along said inside bore of said shape memory needle into a receiving slot of said second needle, and continue passing said suture along said inside bore of said second needle;
   (j) retrieving said suture from said proximal opening of said second needle outside said suture device;
   (k) retracting said hook, leaving said suture between said distal openings of said first needle and said second needle;
   (l) withdrawing said suture device from said site of surgical operation, leaving said suture in said tissue;
   (m) tying and delivering slip knot to said tissue;
   (n) cutting off excess suture; and
   (o) repeating all of the steps a plurality of times until said tissue is fastened.

19. A method of endoscopically suturing tissue in claim 18 and claim 17, wherein said shape memory needle is deployed outside said tissue, a full-thickness suturing is formed.

20. A method of endoscopically suturing tissue in claim 17 and claim 18, wherein said shape memory needle is deployed within said tissue, a partial-thickness suturing is formed.

21. A method of endoscopically suturing tissue in claim 18 and claim 17, wherein said suture further comprises a flexible and pushable filament.

* * * * *